United States Patent [19]

D'Amore

[11] Patent Number: 5,026,901

[45] Date of Patent: Jun. 25, 1991

[54] PALLADIUM CATALYZED CARBOALKOXYLATION OF BUTADIENE

[75] Inventor: Michael B. D'Amore, Wilmington, Del.

[73] Assignee: E. I. Du Pont de Nemours and Company, Wilmington, Del.

[21] Appl. No.: 501,111

[22] Filed: Mar. 29, 1990

[51] Int. Cl.$^5$ ............................................. C07C 67/36
[52] U.S. Cl. .................................................... 560/207
[58] Field of Search .......................................... 560/207

[56] References Cited

U.S. PATENT DOCUMENTS 4,172,087 10/1979 Knifton ................................ 560/207
4,824,817 4/1989 Drent .................................. 560/207

*Primary Examiner*—Paul J. Killos

[57] ABSTRACT

A process for the preparation of linear alkyl pentenoates by reacting butadiene, carbon monoxide and an alkyl alcohol in an organic solvent with a homogeneous catalytic mixture containing five components namely, palladium, chloride, a strong acid, an aryl monodentate phosphine, and a N-heterocyclic base.

10 Claims, No Drawings

PALLADIUM CATALYZED CARBOALKOXYLATION OF BUTADIENE

FIELD OF THE INVENTION

This invention relates to a process for the carboalkoxylation of butadiene, in particular, to a process for the preparation of alkyl pentenoates from 1,3-butadiene.

BACKGROUND OF THE INVENTION

Many processes have been disclosed in which transition metal catalysts are used to carbonylate olefins. In particular, palladium-catalyzed carboalkoxylation reactions have been studied for many years as a means of converting butadiene to adipic acid precursors. Catalyst systems for such processes which comprise palladium and monodentate or multidentate Group V ligands are disclosed in: German Offenlegungsschrift No. 2410246; EP 55,875; EP 273,489; EP 284,170; and U.S. Pat. No. 3,887,595. Catalyst systems which comprise palladium, a Group V ligand, and an acid promoter are disclosed in: U.S. Pat. No. 3,437,676; U.S. Pat. No. 3,501,518; U.S. Pat. No. 4,414,409; U.S. Pat. No. 4,786,443; G.B. 1,110,405; EP 43,382; EP 106,379; EP 198,521; EP 227,160; EP 235,864; EP 271,145; and EP 279,477.

U.S. Pat. No. 4,172,087 discloses a palladium catalyst system consisting of: (a) one or more palladium halide salts in combination with one or more monodentate tertiary phosphorus containing donor ligands, or one or more palladium halide free salts in combination with one or more multidentate, tertiary phosphorus containing donor ligands; (b) at least one molar equivalent of a hydroxyl group containing co-reactant; and (c) a nitrogen-containing base. The preferred starting material is 1,3-butadiene. Pyridine, alkylated pyridines, quinoline, lutidine, picoline, isoquinoline, alkylated quinolines and isoquinolines, acridine, N,N-dimethylaniline, N,N-diethylaniline, N,N-diethyltoluidine, N,N-dibutyltoluidine, N,N-dimethylformamide and N-methyl-2-pyrrolidone can be used as the nitrogen-containing base.

U.S. Pat. No. 3,437,676 discloses a carbonylation process in which an olefinically unsaturated compound is reacted with carbon monoxide and an alcohol to produce a carboxylic acid ester, the reaction being carried out under the influence of a complex palladium salt as a catalyst in an amount of 0.01 to 1% by weight with reference to the olefinically unsaturated compound. Triphenylphosphinepyridine palladium dichloride is a suitable catalyst (Col. 4, lines 3–4). The reaction may be carried out in the presence of an organic or inorganic acid, including sulfuric acid, phosphoric acid, boric acid, acetic acid, propionic acid, other carboxylic acids, or halogen hydracids in amounts up to 10% by weight with reference to the whole of the initial materials (Col. 4, line 63–Col. 5, line 1).

The reactions disclosed in the prior art for the carboalkoxylation of butadiene often proceed at moderate temperatures and pressures, and thus provide attractive routes to dimethyl adipate, a precursor to adipic acid. However, the selectivity to the desired linear products (dialkyl adipates) achieved by these reactions is usually less than 75%, and hence there is a need to develop more selective processes for the carboalkoxylation of butadiene.

It has now been found that a catalyst comprising palladium, chloride, a strong acid, an aryl phosphine, and a N-heterocyclic base can be used in the carboalkoxylation of butadiene to give higher butadiene conversion and greater selectivity to the desired pentenoate esters.

SUMMARY OF THE INVENTION

This invention provides a process for the preparation of alkyl pentenoates, i.e.

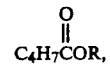

comprising reacting butadiene, carbon monoxide, and an alcohol, i.e. ROH, in the presence of a catalyst comprising palladium, chloride, a strong acid, an aryl phosphine, and a N-heterocyclic base, wherein R is selected from the group of $C_1$ to $C_{12}$ alkyl, the molar ratio of N-heterocyclic base to strong acid is at least 0.5, and the reaction is carried out in a solvent.

DETAILED DESCRIPTION OF THE INVENTION

The process of this invention provides the desired linear pentenoates, i.e., the alkyl esters of cis- and trans-2-pentenoic acid, cis- and trans-3-pentenoic acid, and 4-pentenoic acid, in very high selectivity. These alkyl pentenoates can then be further reacted to give dialkyl adipates or other adipic acid precursors.

The key to achieving both high conversions of butadiene to products and high selectivity to the desired linear products is the use of a catalyst mixture which comprises palladium, chloride, a strong acid, an aryl phosphine, and a N-heterocyclic base. Catalyst mixtures lacking one or more of these five components give significantly lower conversions and/or selectivities than the preferred five-component systems, in which quantitative conversions can be achieved with over 90% selectivity to methyl pentenoates.

The palladium necessary for the reaction can be provided by any palladium compound or salt which is soluble under the reaction conditions and which does not contain components detrimental to the carboalkoxylation reaction. Suitable palladium compounds include $PdX_2(X=Cl, Br, I)$; $Pd(acetate)_2$; $Pd(PPH_3)_4$; $Pd(CO_2CH_3)Cl(PPh_3)_2$; $PdCl_2(PPh_3)_2$, and derivatives thereof. The preferred compounds are $PdCl_2$ and $PdCl_2(PPh_3)_2$. The amount of palladium used in the process of this invention is preferably between 0.005 and 0.5 wt % of the total reaction mixture. The use of lower amounts tends to result in the formation of significant amounts of butadiene oligomers and carboalkoxylated derivatives thereof; the use of higher amounts of palladium is unnecessary and uneconomical.

The catalyst must contain either an organic or inorganic source of chloride. Suitable sources of chloride include acids, palladium compounds, chlorinated hydrocarbons, and inorganic salts, for example, HCl, $PdCl_2$, 3-chloro-1-butene, and chloride-containing salts such as LiCl which are at least partially soluble under the reaction conditions. The preferred source of chloride is $PdCl_2$. The molar ratio of chloride to palladium is preferably about 1 to 10, most preferably about 2 to about 4. The reaction will occur at molar ratios of chloride to palladium less than 1, but at lower rates for a given amount of palladium.

Aryl phosphines suitable for the process of this invention are monodentate phosphines which contain at least one aryl group attached to phosphorus. The aryl group(s) may be unsubstituted or contain one or more $C_1$-$C_4$ alkyl, $C_1$-$C_4$ alkoxy, halo, $SO_3$— or other substituents which are inert under the reaction conditions. Suitable non-aryl groups attached to phosphorus include $C_1$-$C_6$ alkyl and cycloalkyl groups. Preferred phosphines are triphenylphosphine, tris(p-tolyl)phosphine and tris(3-chlorophenyl)phosphine. The molar ratio of phosphine to palladium is preferably about 1 to about 15, most preferably about 4 to about 8.

Strong acids which are suitable for the process of this invention include those with a pKa less than about 3.5, such as HCl, $H_2SO_4$, sulfonic acids such as trifluoromethanesulfonic acid, and substituted benzoic acids such as 2,6-dichlorobenzoic acid and 2,4,6-trimethylbenzoic acid. The molar ratio of strong acid to palladium should be 0.5 to about 10, preferably 1 to 4.

Suitable N-heterocyclic bases have a pKa of at least about 3 and include pyrazine, pyridine, alkyl-substituted pyridines in which the alkyl groups have 1 to 5 carbon atoms, alkoxy-substituted pyridines in which the alkoxy groups have from 1 to 5 carbon atoms, and cycloalkyl-, cycloalkyloxy-, aryl and aryloxy groups having 6 to 14 carbon atoms.

Specific examples of N-heterocyclic bases include:
pyrazine
pyridine
3,4-dimethylpyridine
4-phenoxypyridine
quinoline
isoquinoline
2,2'-bipyridyl
2-picoline
3-picoline
4-picoline
2,3-dimethylpyridine
2,4-dimethylpyridine
3,5-dimethylpyridine
4-benzylpyridine
3-acetylpyridine
2,6-lutidine
4-phenylpyridine The N-heterocyclic base can be used in small amounts (e.g., 0.2 wt %), or can be used as a solvent for the reaction. However, the molar reaction of N-heterocyclic base to strong acid must be at least 0.5, preferably at least 1.

The butadiene used in this process should be substantially free of impurities, although small amounts of unreactive compounds such as butanes and inert gases can be tolerated. The butadiene can be added to the reaction mixture all at once or in incremental amounts. To minimize the formation of butadiene dimers and their derivatives, the concentration of butadiene should be kept below about 30 wt % during the reaction. If the process is operated in a continuous manner, the amount of butadiene in the reaction mixture at any particular time may be very small—less than 1% by weight of the reaction mixture.

The carbon monoxide for this process can be obtained from commercial sources. The carbon monoxide source can contain small amounts of $H_2$ (1–10%, preferably less than 5%), carbon dioxide, saturated hydrocarbons, and other inert gases. The amount of carbon monoxide in the reactor should be at least sufficient to satisfy the stoichiometry of the carbonylation reaction.

Suitable alcohols, i.e. ROH, used in the process of this invention are those in which R is selected from the group of $C_1$ to $C_{12}$ alkyl. Methanol and ethanol are preferred. The preferred molar ratio of alcohol to butadiene is between about 1:1 and 3.0:1. At lower ratios, there is insufficient alcohol to carboalkoxylate all of the butadiene; at higher ratios, significant amounts of dimers and their derivatives are formed, especially when the acid is not HCl.

The process of this invention is not critically dependent on pressure, although the preferred range is between about 1000 and about 10,000 psi.

The reaction is usually carried out at a temperature in the range of between about 80° C. and about 170° C., preferably 90° C. to 170° C. Reactions run at lower temperatures tend to produce significant amounts of dimers and dimeric products; higher temperatures require higher pressures.

A solvent is necessary for this reaction. Suitable solvents include:

Alkanes: pentane; hexane, heptane; octane; cyclohexane; methyl-cyclohexane; 2,2,3-trimethylpentane; gasoline fractions Amides: DMF; N,N-ethylisopropyl formamide; acetamide; N-phenyl acetamide; isobutyramide; isovaleramide; isocaprylamide; N-caprylamide; N-propyl-heptanoylamide; isoundecylamide Aromatics: benzene; toluene; xylenes; mesitylene; ethylbenzene; pentylbenzene; cumene; chlorobenzene; dichlorobenzenes Esters: methyl acetate; ethyl acetate; sec-butyl acetate; cyclohexyl acetate; furfural acetate; ethyl formate; glycol diformate; butyl formate; methyl benzoate; ethyl benzoate; benzobenzoate; ethyl propionate; diethyl oxalate; dibutyl oxalate; dimethylphthalate; dibutyl phthalate; diethyl malonate; methyl salicylate; butyrolactone; valerolactone; dimethyladipate; diethyladipate; di-isopropyladipate, and methylvalerate;

Ethers: diethyl ether; di-isopropyl ether; di-n-butyl ether; di-isobutyl ether; di-isoamyl ether; ethyl benzyl ether; anisole; diphenyl ether; THF; dioxane; methyl-o-tolyl ether; diglyme; ethylene glycol; ethylene glycol dibutyl ether; ethylene glycol di-isoamyl ether; diethylene glycol diethyl ether; diethylene glycol dimethyl ether; ethylene glycol diphenyl ether; triethylene glycol diethyl ether; tetraethylene glycol dimethyl ether; tetraethylene glycol dibutyl ether Halocarbons: methylene chloride; carbon tetrachloride Ketones: acetone; methyl ethyl ketone; methyl isobutyl ketone; acetophenone; acetylacetone; cyclohexanone Nitriles: acetonitrile; benzonitrile N-heterocyclic bases: pyrazine; pyridine; 3,4-dimethylpyridine; 4-phenoxypyridine; quinoline; isoquinoline; 2,2'-bipyridyl; 2-picoline; 3-picoline; 4-picoline; 2,3-dimethylpyridine; 2,4-dimethylpyridine; 3,5-dimethylpyridine; 4-benzylpyridine; 3-acetylpyridine; 2,6-lutidine; 4-phenylpyridine Sulfones: di-isopropyl sulfone; diethyl sulfone; butyl amyl sulfone; methyl benzyl sulfone; sulfolane; 2-methyl sulfolane; 2-methyl-4-butyl sulfolane Sulfoxides: dimethylsulfoxide Preferred solvents are dimethyladipate, pyridine, diphenylether, methylvalerate and dimethyl pimalate.

The process of this invention can be carried out in batch or continuous mode.

The following examples are presented to illustrate, but not to restrict, the present invention. Parts and percentages are by weight and temperatures are in degrees Celsius unless otherwise noted.

EXAMPLES

In a typical procedure, a Pyrex ® glass liner was charged with 0.12 g $PdCl_2$ (0.68 mmole), 1.00 g triphenylphosphine (3.81 mmole), 1.00 g pyridine (12.6 mmole), 0.25 g sulfuric acid (2.55 mmole), 4.0 g methanol (125 mmole) and 20.0 g dimethyladipate. The liner was inserted into a Hastelloy shaker tube and cooled to −78° C. and evacuated. Butadiene (6 g, 111 mmole) was condensed into the tube. The tube was pressured to 2000 psi with carbon monoxide at room temperature, heated to 140° C. and the pressure maintained at 3500 psig. After 3 hours, the tube was cooled and the contents were analyzed by gas chromatography. The results of this example and similar examples run using this basic procedure are given in Table 1.

Examples of the Invention

| Ex. | T (°C.) | P (psig) | Time (h) | Py (g) | Solv., wt. (g) | $Pd^1$ (g) | Phos (g) | MeOH (g) | $Acid^2$ (g) | BD (g) | BD Conv. | Prod. MP | Select. (%) DBE | Dimer |
|---|---|---|---|---|---|---|---|---|---|---|---|---|---|---|
| 1 | 150 | 5,000 | 3 | 10 | DPE, 15 | 0.14 | 1 | 9 | 0.5 | 6 | 96 | 85 | 6 | 6 |
| 2 | 150 | 5,000 | 3 | 10 | DPE, 15 | 0.14 | 1 | 9 | $0.46^3$ | 6 | 76 | 80 | 13 | 3 |
| 3 | 150 | 5,000 | 3 | 10 | MVAL, 15 | 0.14 | 1 | 9 | 0.5 | 6 | 100 | 84 | 13 | 2 |
| 4 | 150 | 5,000 | 3 | 10 | DMP, 15 | 0.14 | 1 | 9 | 0.5 | 6 | 100 | 89 | 2 | 6 |
| 5 | 140 | 3,600 | 3 | 20 | — | 0.07 | 1 | 9 | 0.5 | 7 | 90 | 85 | 0 | 12 |
| 6 | 140 | 3,000 | 3 | 20 | — | 0.12 | 1 | 4 | 0.5 | 6 | 100 | 80 | 0 | 20 |
| 7 | 140 | 3,500 | 3 | 1 | DMA, 20 | 0.12 | 1 | 4 | 0.25 | 6 | 86 | 90 | 4 | 4 |
| 8 | 140 | 3,500 | 3 | 0.5 | DMA, 20 | 0.12 | 1 | 4 | 0.13 | 6 | 100 | 90 | 5 | 3 |
| 9 | 140 | 3,500 | 3 | 0.25 | DMA, 20 | 0.12 | 1 | 4 | 0.06 | 6 | 89 | 87 | 4 | 6 |
| 10 | 130 | 3,500 | 3 | 0.5 | DMA, 20 | 0.12 | 1 | 4 | 0.13 | 6 | 88 | 89 | 3 | 6 |
| 11 | 155 | 5,000 | 1 | 1 | DMA, 20 | 0.12 | 1 | 4 | 0.25 | 6 | 80 | 91 | 2 | 4 |
| 12 | 140 | 3,500 | 3 | 1 | DMA, 20 | 0.12 | 1 | 2.4 | 0.13 | 4 | 100 | 92 | 1 | 4 |
| 13 | 140 | 3,500 | 3 | $0.34^4$ | DMA, 20 | 0.12 | 1 | 4 | 0.13 | 6 | 75 | 82 | 1 | 12 |
| 14 | 140 | 3,500 | 3 | $0.82^5$ | DMA, 20 | 0.12 | 1 | 4 | 0.13 | 6 | 66 | 91 | 3 | 3 |
| 15 | 140 | 3,500 | 3 | $0.77^6$ | DMA, 20 | 0.12 | 1 | 4 | 0.13 | 6 | 74 | 86 | 6 | 5 |
| 16 | 140 | 3,500 | 3 | $1.0^7$ | DMA, 20 | 0.12 | 1 | 4 | 0.25 | 6 | 59 | 85 | 1 | 9 |
| 17 | 140 | 3,500 | 3 | $1.0^8$ | DMA, 20 | 0.12 | 1 | 4 | 0.13 | 6 | 79 | 85 | 7 | 5 |
| 18 | 140 | 3,500 | 3 | 1 | DMA, 20 | $0.49^9$ | 0.65 | 4 | 0.25 | 6 | 66 | 85 | 1 | 10 |
| 19 | 140 | 3,500 | 6 | 1 | DMA, 20 | 0.12 | 1 | 4 | 0.25 | 6 | 91 | 88 | 5 | 5 |
| 20 | 140 | 3,500 | 3 | $1.35^{10}$ | DMA, 20 | 0.12 | 1 | 4 | 0.25 | 6 | 82 | 89 | 5 | 4 |
| 21 | 140 | 3,500 | 3 | $1.17^{11}$ | DMA, 20 | 0.12 | 1 | 4 | 0.25 | 6 | 89 | 88 | 5 | 4 |
| 22 | 140 | 3,500 | 3 | 1 | DMA, 20 | 0.12 | $1.16^{12}$ | 4 | 0.25 | 6 | 82 | 87 | 1 | 9 |
| 23 | 140 | 3,500 | 3 | 1 | DMA, 20 | 0.12 | $1.39^{13}$ | 4 | 0.25 | 6.3 | 98 | 91 | 4 | 3 |
| 24 | 140 | 3,500 | 3 | 1 | DMA, 20 | 0.12 | 1 | 4 | $0.42^{14}$ | 6 | 72 | 80 | 1 | 14 |
| 25 | 140 | 3,500 | 3 | 1 | DMA, 20 | 0.12 | 1 | 4 | $0.38^{15}$ | 6 | 84 | 76 | 15 | 7 |

Footnotes
[1] "Pd" = Pd(acetate)$_2$ in Ex. 1–5; "Pd" = PdCl$_2$ in Ex. 6–25, unless otherwise noted.
[2] "Acid" = 35% eq. HCl in Ex. 1–5; "Acid" = H$_2$SO$_4$ in Ex. 6–25, unless otherwise noted.
[3] 3-Chloro-1-butene
[4] 2,6-Lutidine
[5] Isoquinoline
[6] 3-Acetylpyridine
[7] Pyrazine
[8] 4-Phenylpyridine
[9] PdCl(CO$_2$CH$_3$)(Ph$_3$P)$_2$
[10] 3,5-Lutidine
[11] 3-Picoline
[12] (p-Tolyl)$_3$P
[13] (3-Chlorophenyl)$_3$P
[14] 2,4,6-Trimethylbenzoic acid
[15] CF$_3$SO$_3$H
"DPE" = diphenylether
"MVAL" = methylvalerate
"DMP" = dimethylpimelate
"DMA" = dimethyladipate
"Py" = Pyridine, unless otherwise noted
"Phos" = Triphenylphosphine, unless otherwise noted
"BD" = 1,3-Butadiene
"MP" = Methyl pentenoates
"DBE" = Dibasic esters
"Dimer" = Butadiene dimers and carbonylated derivatives "BD Conv." = $\frac{\text{Moles of Products}}{\text{Moles of BD charged}} \times 100$ "Select." = $\frac{\text{Moles of a given Product}}{\text{Moles of combined Products}} \times 100$

I claim:

1. A process for the preparation of linear alkyl pentenoates which comprises reacting butadiene, carbon monoxide, and an alkyl alcohol in an organic solvent, with a homogeneous catalytic mixture comprising palladium, chloride, a strong acid, an aryl monodentate phosphine, and a N-heterocyclic base, at a temperature in the range of between about 80 and 170 degrees C. in which palladium is present in the reaction mixture in the amount of about 0.005 to 0.5 weight % of the reaction mixture, in which the chloride to palladium molar ratio is in the range of 1 to 10, in which the aryl monodentate phosphine to palladium molar ratio is greater than 1 and less than about 15, in which the strong acid has a pKa of less than 3.5, and the molar ratio of strong acid to palladium is in the range of 0.5 to 10, in which the N-heterocyclic base has a pKa of at least about 3 and the N-heterocyclic base is present in a molar ratio to strong acid of at least 0.5, and in which the alkyl alcohol has 1 to 12 carbon atoms and the alcohol to butadiene ratio is 1:1 to 3:1, and carbon monoxide is present in an amount at least sufficient to satisfy the stoichiometry of the carbonylation reaction.

2. The process of claim 1 in which the strong acid is selected from the class consisting of hydrochloric acid, sulfuric acid, sulfonic acid and substituted benzoic acid.

3. The process of claim 2 in which the acid is a sulfonic acid and the sulfonic acid is trifluoromethanesulfonic acid.

4. The process of claim 2 in which the acid is a benzoic acid and the benzoic acid is 2,4,6-trimethylbenzoic acid.

5. The process of claim 1 in which the N-heterocyclic base is selected from the class consisting of pyridine, and alkyl-substituted pyridine in which the alkyl groups have 1 to 5 carbon atoms, alkoxy-substituted pyridines in which the alkoxy groups have from 1 to 5 carbon atoms, and cycloalkyl-, cycloalkyloxy-, aryl and aryloxy groups having 6 to 14 carbon atoms.

6. The process of claim 5 in which the N-heterocyclic base is an alkyl-substituted pyridine and the alkyl-substituted pyridine is selected from the class consisting of 2,6-lutidine, 3,5-lutidine and 3-picoline.

7. The process of claim 1 in which the organic solvent is selected from the class consisting of alkanes, amides, aromatics, esters, ethers, halocarbons, ketones, nitriles, sulfones, sulfoxides, and N-heterocyclic bases.

8. The process of claim 1 in which the organic solvent is selected from the class consisting of dimethyladipate, diethyladipate, diphenylether, methyl valerate, and pyridine.

9. The process of claim 1 in which the aryl monodentate phosphine contains at least one aryl group attached to phosphorus.

10. The process of claim 9 in which the aryl monodentate phosphine is selected from the class consisting of triphenylphosphine, tris(3-chlorophenyl)phosphine, and tris(p-tolyl)phosphine.

* * * * *